US009097623B2

(12) United States Patent
Silvis et al.

(10) Patent No.: US 9,097,623 B2
(45) Date of Patent: Aug. 4, 2015

(54) CVS SYSTEM SAMPLE WATER VAPOR MANAGEMENT

(75) Inventors: William Martin Silvis, Ann Arbor, MI (US); James Williamson, Pinckney, MI (US)

(73) Assignee: AVL Test Systems, Inc., Plymouth, MI (US)

( * ) Notice: Subject to any disclaimer, the term of this patent is extended or adjusted under 35 U.S.C. 154(b) by 444 days.

(21) Appl. No.: 13/463,226

(22) Filed: May 3, 2012

(65) Prior Publication Data

US 2012/0210803 A1     Aug. 23, 2012

Related U.S. Application Data

(63) Continuation of application No. 12/501,767, filed on Jul. 13, 2009, now Pat. No. 8,181,543, which is a continuation-in-part of application No. 11/855,246, filed on Sep. 14, 2007, now Pat. No. 7,559,262.

(60) Provisional application No. 60/845,271, filed on Sep. 15, 2006.

(51) Int. Cl.
     *G01N 1/22*         (2006.01)
     *G01M 15/10*      (2006.01)
     *G01N 1/24*         (2006.01)

(52) U.S. Cl.
CPC ........... *G01N 1/2252* (2013.01); *G01M 15/102* (2013.01); *G01N 2001/2255* (2013.01); *G01N 2001/2264* (2013.01)

(58) Field of Classification Search
CPC .............. G01M 15/102; G01N 1/2252; G01N 2001/2255; G01N 2001/2264
USPC ................. 73/23.31, 863.02–863.11, 863.58, 73/863.81, 863.83, 863.86, 864.62
See application file for complete search history.

(56) References Cited

U.S. PATENT DOCUMENTS

| | | |
|---|---|---|
| 3,603,155 A | 9/1971 | Morris et al. |
| 3,610,047 A | 10/1971 | List et al. |
| 3,699,814 A * | 10/1972 | Kaufman .................... 73/863.11 |
| 3,793,887 A | 2/1974 | Anderson et al. |
| 4,040,783 A | 8/1977 | Collin |
| 5,058,440 A * | 10/1991 | Graze, Jr. ................... 73/863.83 |

(Continued)

FOREIGN PATENT DOCUMENTS

| | | | |
|---|---|---|---|
| DE | 4017473 A1 * | 11/1991 | ............ G01M 15/10 |
| EP | 42800 | 12/1981 | |

(Continued)

*Primary Examiner* — Thomas P Noland
(74) *Attorney, Agent, or Firm* — Harness, Dickey & Pierce, P.L.C.

(57) ABSTRACT

An exhaust sampling system includes a pre-fill gas source having a pre-fill gas. A sampling conduit is configured to collect exhaust gas and make-up gas. A sample bag is fluidly connected to the sampling conduit and the pre-fill gas source. A controller is programmed to run a test procedure in which a sample of exhaust gas and make-up gas is collected in the sample bag. The controller sends a command that fills the sample bag with pre-fill gas prior to the test procedure. The pre-fill gas remains in the sample bag during the test procedure. In one example, the amount of pre-fill gas is selected to prevent the sample from condensing in the sample bag during the test procedure. In another example, the amount of pre-fill gas is selected to provide a sufficient volume of gases for analysis during the test procedure.

14 Claims, 4 Drawing Sheets

(56) References Cited

U.S. PATENT DOCUMENTS

| | | | |
|---|---|---|---|
| 5,456,124 | A | 10/1995 | Colvin |
| 5,546,788 | A * | 8/1996 | Dickow .............. G01M 15/102 |
| 5,650,565 | A | 7/1997 | Nagy et al. |
| 5,821,435 | A | 10/1998 | Kojima |
| 6,016,711 | A * | 1/2000 | Ullman et al. ............. 73/863.03 |
| 6,134,942 | A * | 10/2000 | Pasquereau et al. ......... 73/23.31 |
| 6,282,944 | B1 | 9/2001 | Bornemann |
| 6,370,936 | B1 * | 4/2002 | Yamagishi et al. .... 73/863.03 X |
| 6,405,577 | B2 | 6/2002 | Hanashiro et al. |
| 6,412,333 | B2 | 7/2002 | Inoue et al. |
| 6,443,021 | B2 | 9/2002 | Hanashiro et al. |
| 6,470,732 | B1 * | 10/2002 | Breton ........................ 73/23.31 |
| 6,490,937 | B2 | 12/2002 | Hanashiro et al. |
| 6,497,156 | B2 | 12/2002 | Dageforde |
| 6,578,440 | B2 | 6/2003 | Lewis |
| 7,559,262 | B2 | 7/2009 | Silvis et al. |
| 2001/0003915 | A1 * | 6/2001 | Inoue et al. .......... G01N 1/2252 |
| 2003/0093943 | A1 | 5/2003 | Jordan |
| 2003/0149536 | A1 | 8/2003 | Silvis et al. |
| 2004/0139785 | A1 * | 7/2004 | Abdul-Khalek ..... G01N 1/2252 |
| 2004/0226354 | A1 * | 11/2004 | Schmidt ................... 73/23.31 X |
| 2005/0109128 | A1 * | 5/2005 | Pasquereau et al. ..... G01N 1/22 |
| 2005/0160838 | A1 | 7/2005 | Weaver |
| 2006/0243026 | A1 * | 11/2006 | Graze et al. .................. 73/23.31 |
| 2010/0000339 | A1 * | 1/2010 | Silvis et al. .......... G01N 1/2252 |
| 2011/0252864 | A1 | 10/2011 | Guenther et al. |

FOREIGN PATENT DOCUMENTS

| | | | | |
|---|---|---|---|---|
| EP | 610523 | A1 * | 8/1994 | ............... G01N 1/24 |
| EP | 928962 | A1 * | 7/1999 | ............... G01N 1/22 |
| EP | 973080 | A2 * | 1/2000 | ............... G05D 7/06 |
| JP | 07035660 | | 5/1995 | |
| JP | 10318810 | | 12/1998 | |
| JP | 11344425 | | 12/1999 | |
| JP | 2000180315 | | 6/2000 | |
| JP | 2000292321 | A * | 10/2000 | ............... G01N 1/22 |
| JP | 2001004504 | | 1/2001 | |
| JP | 2006105024 | | 4/2006 | |
| WO | WO 0014506 | A1 * | 3/2000 | ............... G01N 1/22 |
| WO | WO 0190741 | A2 * | 11/2001 | ........... G01N 1/2252 |

\* cited by examiner

CVS SYSTEM SAMPLE WATER VAPOR MANAGEMENT

The present disclosure is a continuation of U.S. patent application Ser. No. 12/501,767, filed 13 Jul. 2009 now U.S. Pat. No. 8,181,543, which is a continuation-in-part of U.S. patent application Ser. No. 11/855,246 (now U.S. Pat. No. 7,559,262), filed 14 Sep. 2007, which claims the benefits of U.S. Provisional Application No. 60/845,271, filed 15 Sep. 2006. These disclosures are incorporated herein in their entirety by reference.

BACKGROUND

With traditional constant volume samplers (CVS), engine exhaust is diluted with ambient air, and a small sample of the diluted exhaust is proportionally extracted and stored in one or more sample bags. Depending upon the engine size, drive cycle and ambient conditions, the CVS total flow rate, which includes both ambient air and engine exhaust, is selected to ensure the sample collected does not condense water when stored in the bags, or during subsequent analysis. This flow rate is determined by calculating the average dew point in the bag sample.

It is desirable to avoid water condensation within the sample bag for several reasons. First, condensation of water impacts the accuracy of the exhaust analysis. Some substances in the exhaust become soluble in water. These substances can be effectively "pulled out" of the exhaust so that they are not measured at the conclusion of the test. Also, the water vapor that becomes condensed is not measured and included in the test results. Second, the condensation can cause the collection of substances on the inside of the bag as the water subsequently evaporates thereby leaving an undesirable residue that will be present during future tests. Finally, new legislation requires no condensation in the sample bags.

There are several factors that make it difficult to avoid condensation of the sample within the bags. For example, use of alternative fuels, new test cycles and larger displacement engines all can lead to condensation within the sample bags. For example, if an aggressive test cycle is performed and the traditional optimal flow CVS flow rate is selected, then condensation will form. This is particularly true for test cycles where the maximum exhaust comes very early in the collection of the sample. The dew point of the sample may be higher than ambient conditions even though the average water concentration in the bag is less than ambient at the end of the cycle. CVS optimal flow rate is selected to ensure the average water concentration in the bags has a dew point less than ambient temperature.

One potentially problematic test is the newly proposed US06 drive cycle. The cycle is 600 seconds long and the second sample bag used in the test will start filling 133 seconds into the drive cycle. The traditional desired flow rate is 1050 scfm when diluting a gas with a dew point of 18 deg C. For vehicles running on ethanol fuel, the ending dew point in the bag will be just above 23 deg C., with a peak dew point at the beginning of the second bag fill of 27 deg C. This is often higher than ambient conditions in a test cell. In this scenario, the CVS flow rate would typically be selected to dilute for the average bag dew point of 23 deg C., which would result in the sample condensing in the second sample bag due to the initial high peak.

In order to avoid condensation in the bag, the CVS flow rate would have to be raised to 2000 scfm to avoid the initial peak, which is undesirable. Increasing the CVS flow rate would reduce the already low concentration of exhaust within the sample making it more difficult to analyze. One approach that can be used to avoid condensation is to heat the bags, which would maintain the sample gas temperature above the maximum dew point and avoid the initial dew point peak. However, additional equipment must be employed for such an approach leading to a higher cost CVS.

Hybrid vehicles pose unique problems when trying to determine mass emissions rates during emission test sequences. Current test procedures require bag sampling using either a CVS method or a bag mini-diluter (BMD) method. Hybrid vehicles that produce exhaust gas from internal combustion engines may not be in operation or may operate for a brief period of time over the test cycle. When using the CVS method the CVS bag sample is overdiluted and determination of mass emissions is difficult since the dilution factor from the CVS method is very high. When using the BMD method the bag sample is diluted at a fixed rate so the dilution factor issue is resolved but the sample is collected proportional to the exhaust flow. Since there are periods of operation where either no exhaust flow is expelled out of the hybrid vehicle or the vehicle exhaust is expelled intermittently very little exhaust may be emitted during the sample phase. Therefore, very little sample will be collected in the sample bag making accurate analysis more difficult.

SUMMARY

A disclosed method of collecting an exhaust gas sample includes pre-filling a sample bag with a pre-fill gas. An exhaust sample is collected in the sample bag with the pre-fill gas remaining in the sample bag.

An exhaust sampling system is disclosed that includes a pre-fill gas source having a pre-fill gas. A sampling conduit is configured to collect exhaust gas and make-up gas. A sample bag is fluidly connected to the sampling conduit and the pre-fill gas source. A controller is programmed to run a test procedure in which a sample of exhaust gas and make-up gas is collected in the sample bag. The controller is configured to send a command that fills the sample bag with pre-fill gas prior to the test procedure. The pre-fill gas remains in the sample bag during the test procedure. In one example, the amount of pre-fill gas is selected to prevent the sample from condensing in the sample bag during the test procedure. In another example, the amount of pre-fill gas is selected to provide a sufficient volume of gases for analysis during the test procedure.

These and other features of the disclosure can be best understood from the following specification and drawings, the following of which is a brief description.

DETAILED DESCRIPTION

Figure 1:
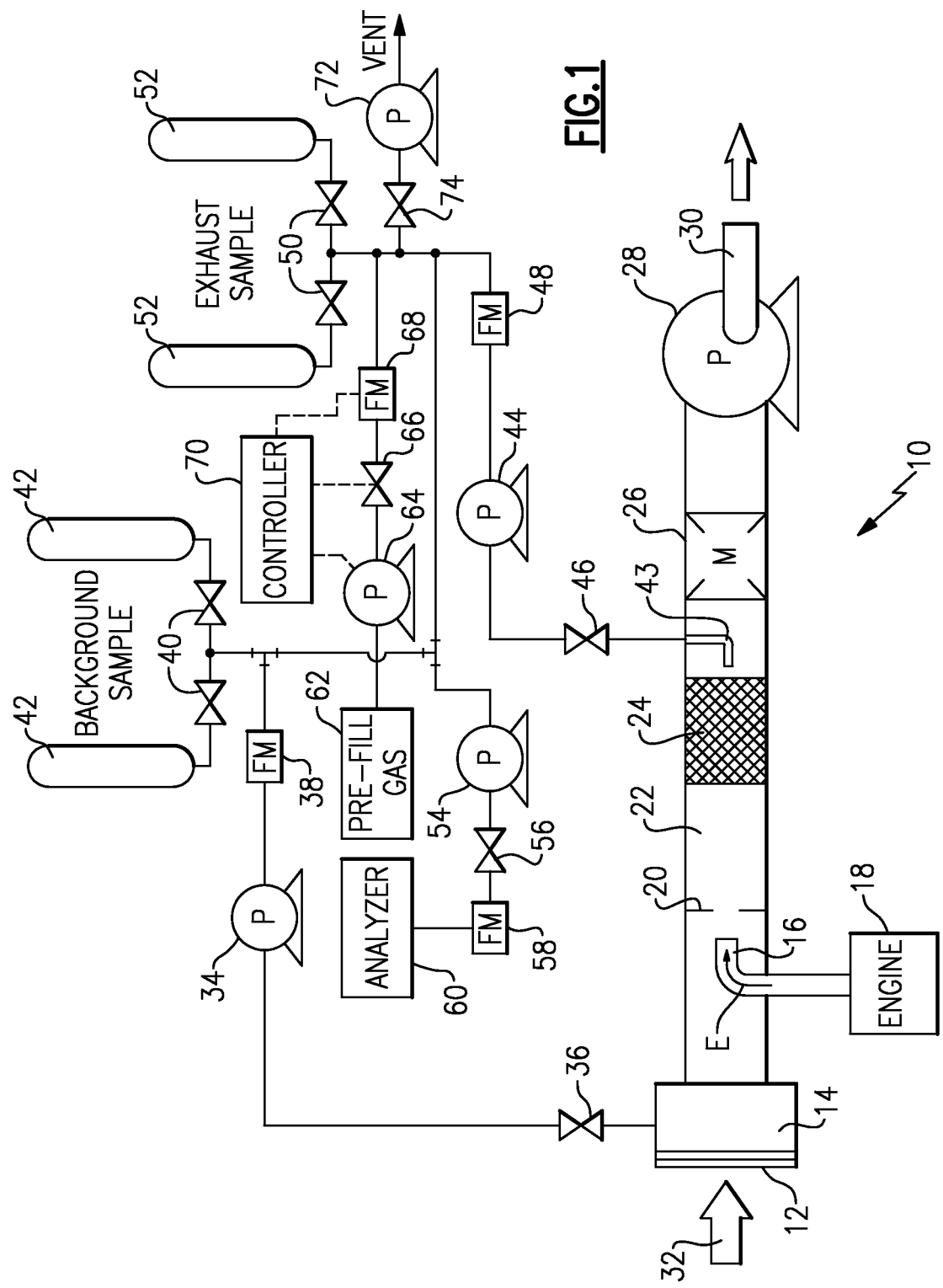
FIG. 1 is a schematic view of an example CVS including an example pre-fill gas system.

A schematic view of an exhaust sampling system 10 is shown in FIG. 1. In this disclosure, like numerals are used to indicate like elements. The system 10 includes a make-up air inlet 12 that includes a filter 14. The inlet 12 provides make-up air 32 to a sampling conduit that also receives exhaust from a tailpipe 16 of an engine 18. The make-up air 32 and exhaust E pass through a mixing plate 20 to promote homogeneous mixing of the make-up air 32 and exhaust E as it flows through a tunnel 22 prior to sampling. A constant volume of the mixture is drawn through the sampling conduit by a pump 28. A heat exchanger 24 is used, in one example, to maintain the mixture at a desired temperature. The mixture is measured by a measuring device 26, prior to being expelled by the pump 28 through a discharge 30, to determine the quantity of mixture flowing through the sampling conduit. It should be understood that the system 10 is only exemplary and that many modifications can be made and still fall within the scope of the claims.

The engine 18 is run through a test procedure to determine the quantity of exhaust byproducts that the engine 18 produces. For the example system 10 shown, only a small portion of the exhaust E is sampled for subsequent analysis. As the amount of exhaust E produced by the engine 18 during the test procedure fluctuates, the make-up air 32 provides the remainder of the volume. The amount of byproducts in the sample is so small at times, that the components in the make-up air can impact the test results. To this end, a pump 34 draws an amount of make-up air into background bags 42 during the test procedure so that the effects of the make-up air can be taken into account. Valves 36, 40 regulate the flow of make-up air 32 into the background bags 42, and the flow meter 38 measures the amount of make-up air collected within the background bags 42.

A sampler 43 collects a small sample of the mixture for collecting into sample bags 52. One or more sample bags 52 may be used, and filling of the sample bags may be scheduled during various periods of the test procedure. A pump 44 draws the sample through a valve 46 and flow meter 48. Valves 50 regulate the filling of the sample bags 52. After the sample bags 52 have collected the samples, an analyzer 60 analyzes the contents of the sample bags 52 and 42 to determine the amount of various combustion byproducts. A pump 54 flows the sample through valve 56 and flow meter 58. It should be understood that more or fewer pumps, valves and flow meters than shown could be used.

A controller 70 communicates during the test procedure with the various pumps 28, 34, 54, 64, 72, valves 36, 40 46, 50, 56, 66, 74 and flow meters 38, 48, 58, 68 to obtain readings and direct their operation. All of the connections between the controller 70 and these components are not shown for clarity.

In one example of this disclosure, one or more of the sample bags 52 is pre-filled with dry gas to prevent any peaks in dew point during the test procedure that would lead to undesired condensation. A source of pre-fill gas 62 is shown schematically in FIG. 1. An amount of pre-fill gas is pumped into one or more of the sample bags 52 prior to the collection of the exhaust sample. The controller 70 commands the pump 64 and valve 66 to fill a desired amount of pre-fill gas to a desired sample bag 52 to prevent condensation in the sample bag 52. The pre-fill may also incorporate other means to fill the bag such as a compressed air source. The flow meter 68 measures the amount of pre-fill gas.

Figure 2:
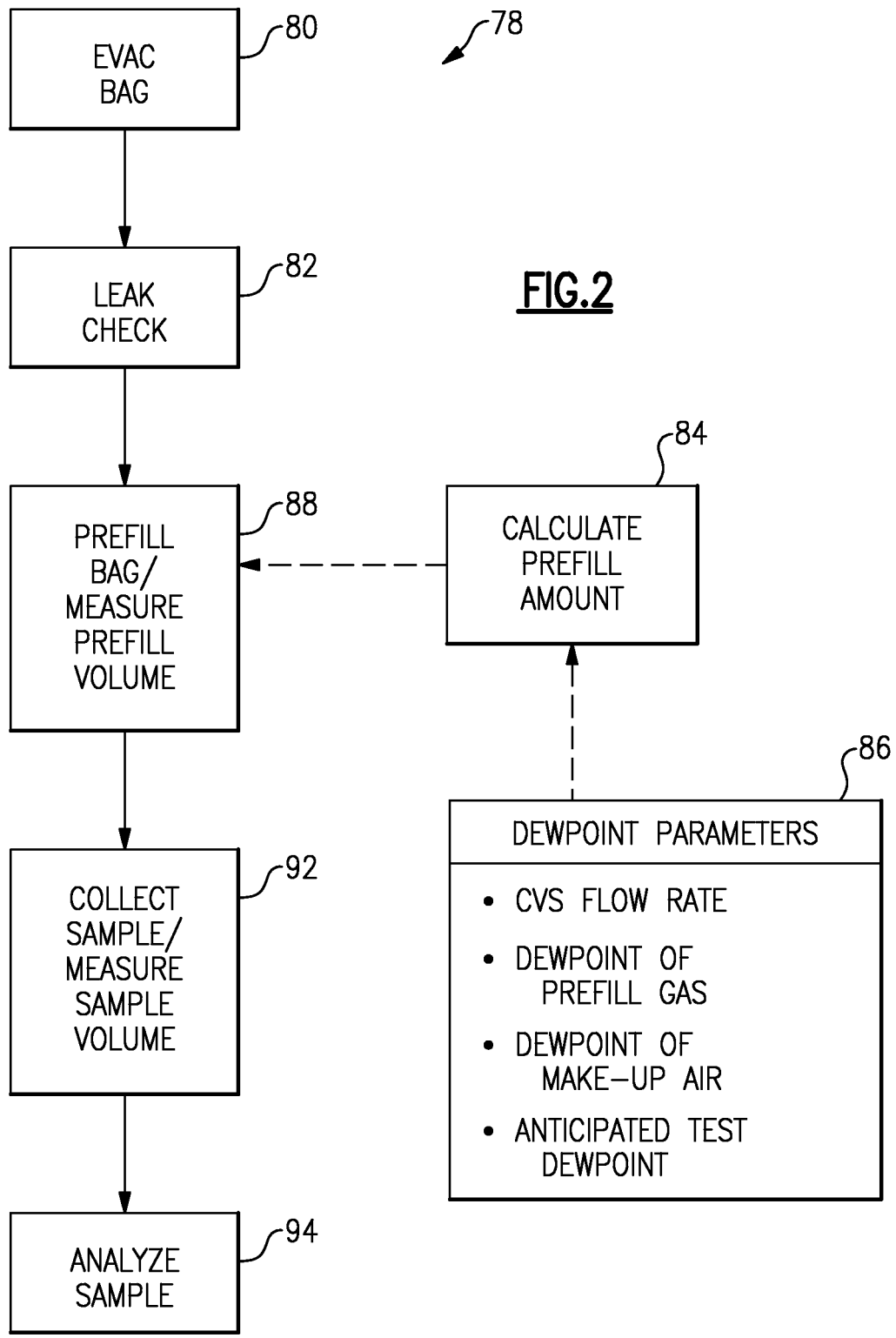
FIG. 2 is a flow chart depicting an example pre-fill procedure.

An example test procedure 78 according to the disclosure is shown in FIG. 2. The amount of pre-fill gas needed to prevent condensation is calculated at block 84 based upon one or more of the following (indicated at block 86): CVS test flow rate, dew point of the pre-fill gas, dew point of the make-up air, and anticipated test dew point within the sample bag 52. Calculations are performed based upon the various factors of each test to determine the minimum amount of pre-fill gas required to avoid condensation. This approach is desirable to minimize further dilution of the sample. The bags susceptible to condensation would be filled with dry clean air prior to the sampling (filling of the bag). According to this disclosure, the initial peak of wet gas is compensated for by the dry air, thus preventing condensation.

The sample bags 52 and ambient bags 42, as well as any intervening conduits, are evacuated through vent 74 using pump 72 (FIG. 1), as indicated at block 80. The system 10 is leak checked (block 82), and the sample bag 52 is filled with a predetermined amount of pre-fill gas, as indicated at block 88. The amount of pre-fill gas is measured. The exhaust sample is collected and its mass and/or volume measured in the sample bag 52 during the test procedure with the pre-fill gas remaining in the sample bag 52, as indicated at block 92. As the sample bag 52 is filled during the test procedure, the dew point of the predetermined amount of pre-fill gas prevents the exhaust sample from condensing within the sample bag 52. The contents of the sample bag 52 and ambient bag 42 can then be analyzed to determine the amount of byproducts within the sample, as indicated at block 94.

In one example, the same "zero grade" or "instrument grade" air that is typically used to initially calibrate the system 10 can be used to pre-fill the sample bag 52. As a result, the pre-fill feature can be incorporated into a traditional CVS with very little modification and expense. Alternatively, ambient air can be used to pre-fill the sample bag 52. Using ambient air may be desirable since it makes accounting for the pre-fill air's affects at the analysis stage of the test simpler. The analytical equations set forth in the Code of Federal Regulations for test procedures are such that accounting for pre-fill ambient air is more straightforward. Using zero grade air instead of ambient air requires modifications to those equations, which may be undesired by some customers. For example, using zero air requires using dilution ratio equations similar to those used for a BMD to determine the concentration necessary to use traditional CVS equations. It should be understood that any number of suitable substances may be used to pre-fill the sample bags 52.

Figure 3:
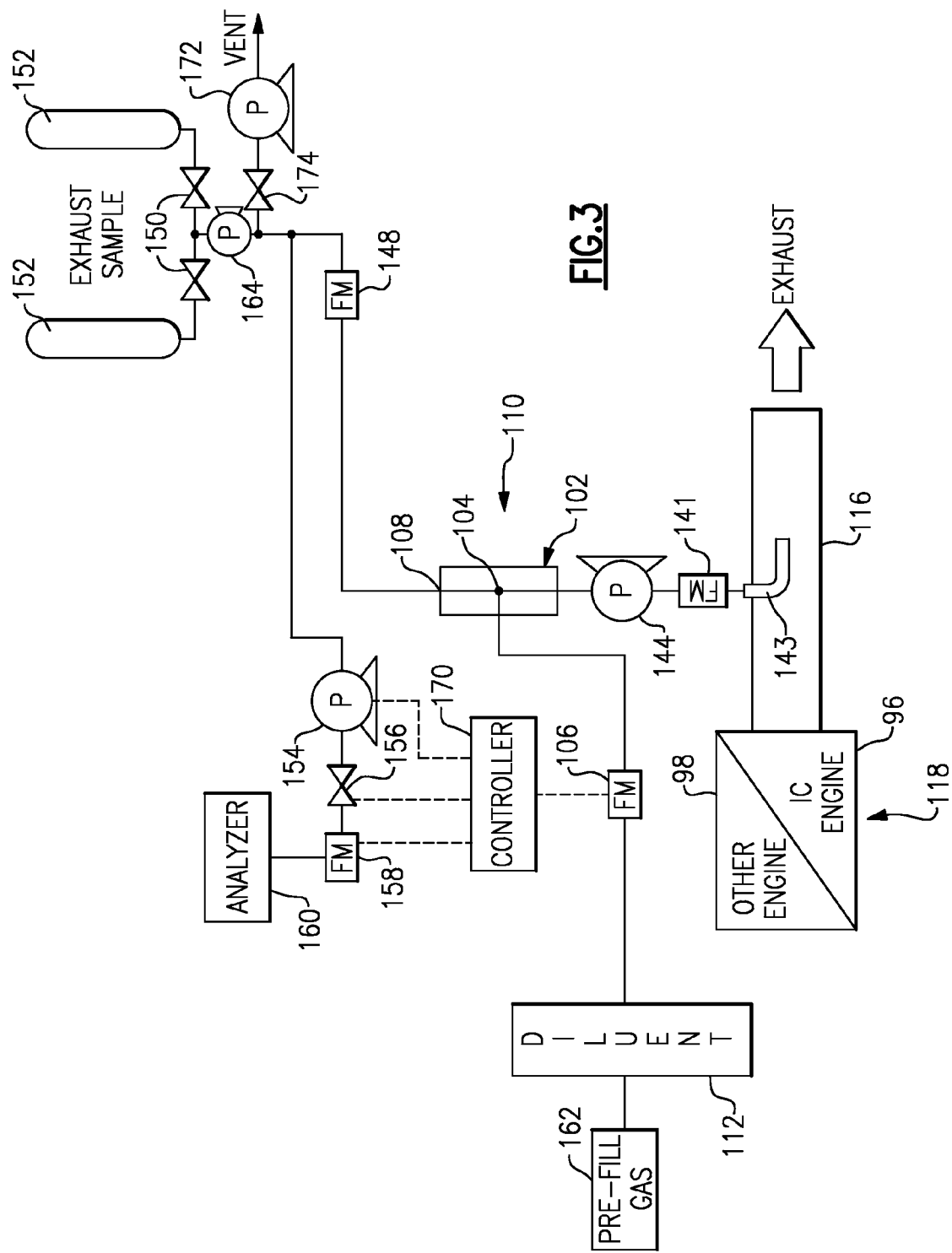
FIG. 3 is a schematic view of an example BMD including an example pre-fill gas system.

A schematic view of another exhaust sampling system 110 is shown in FIG. 3. The system 110 illustrates a BMD sampling system in which the exhaust sample is diluted at a fixed rate and the exhaust gas sample is collected in proportion to the exhaust flow from the engine 118. In the example, the engine 118 includes an internal combustion engine 96 and another engine 98 (such as an electric motor) that together comprise the propulsion unit for a hybrid vehicle. The other engine 98 may be used to propel the vehicle in varying degrees throughout vehicle operation. As a result, there may be periods of operation when the engine 118 expels little or no exhaust through its tailpipe 116 when the other engine 98 is in use.

The system 110 includes a "mini-diluter" having a probe or sampler 143. The sampler 143 collects a small sample of exhaust gas from the tailpipe 116. The sample exhaust gas is drawn into a sampling unit 102 by a pump 144. The sampling unit 102 includes a mixer 104. A diluent 112 is introduced to the sampling unit 102 at the mixer 104 where it commingles with the sample exhaust gas to produce a diluted exhaust gas that is supplied to a diluted exhaust gas outlet 108. In one example, the diluent 112 is nitrogen or zero air. The diluent 112 is measured by a flowmeter 106. The sample exhaust gas flow corresponds to a difference between a total exhaust gas flow measured by a flowmeter 148, which receives the diluted exhaust gas from the outlet 108, and the flowmeter 106. In the example shown, the exhaust gas sample is measured directly by a flowmeter 141.

The engine 118 is run through a test procedure to determine the quantity of exhaust byproducts that the engine 118 produces. For the example system 110 shown, only a small portion of the exhaust is sampled for subsequent analysis. As the amount of exhaust produced by the engine 118 during the test procedure fluctuates, the diluent 112 provides the remainder of the volume.

The sampler 143 collects a small sample of the mixture for collecting into sample bags 152. One or more sample bags 152 may be used, and filling of the sample bags may be scheduled during various periods of the test procedure. Valves 150 regulate the filling of the sample bags 152. After the sample bags 152 have collected the samples, an analyzer 160 analyzes the contents of the sample bags 152 to determine the amount of various combustion byproducts. A pump 154 flows the sample through valve 156 and flow meter 158. It should be understood that more or fewer pumps, valves and flow meters than shown could be used.

A controller 170 communicates during the test procedure with the various pumps 128, 154, 164, 172, valves 150, 156, 174 and flow meters 106, 148, 158 to obtain readings and direct their operation. All of the connections between the controller 170 and these components are not shown for clarity.

In one example of this disclosure, one or more of the sample bags 152 is pre-filled with dry gas to provide a sufficient volume of gases in the bags 152 for subsequent analysis. A source of pre-fill gas 162 is shown schematically in FIG. 3. A common nitrogen source can be used for both the diluent 112 and the pre-fill gas 162. In an example, the pre-fill gas 162 is nitrogen. An amount of pre-fill gas is pumped into one or more of the sample bags 152 prior to the collection of the exhaust sample. The controller 170 commands the pump 164 to fill a desired amount of pre-fill gas to a desired sample bag 152 to sufficiently fill the sample bag 152, discussed in more detail below. The pre-fill may also incorporate other means to fill the bag such as a compressed air source. The flow meter 106 measures the amount of pre-fill gas. Using the same flow meter 106 to measure the pre-fill gas and the diluent during the test procedure minimizes calibration error.

Figure 4:
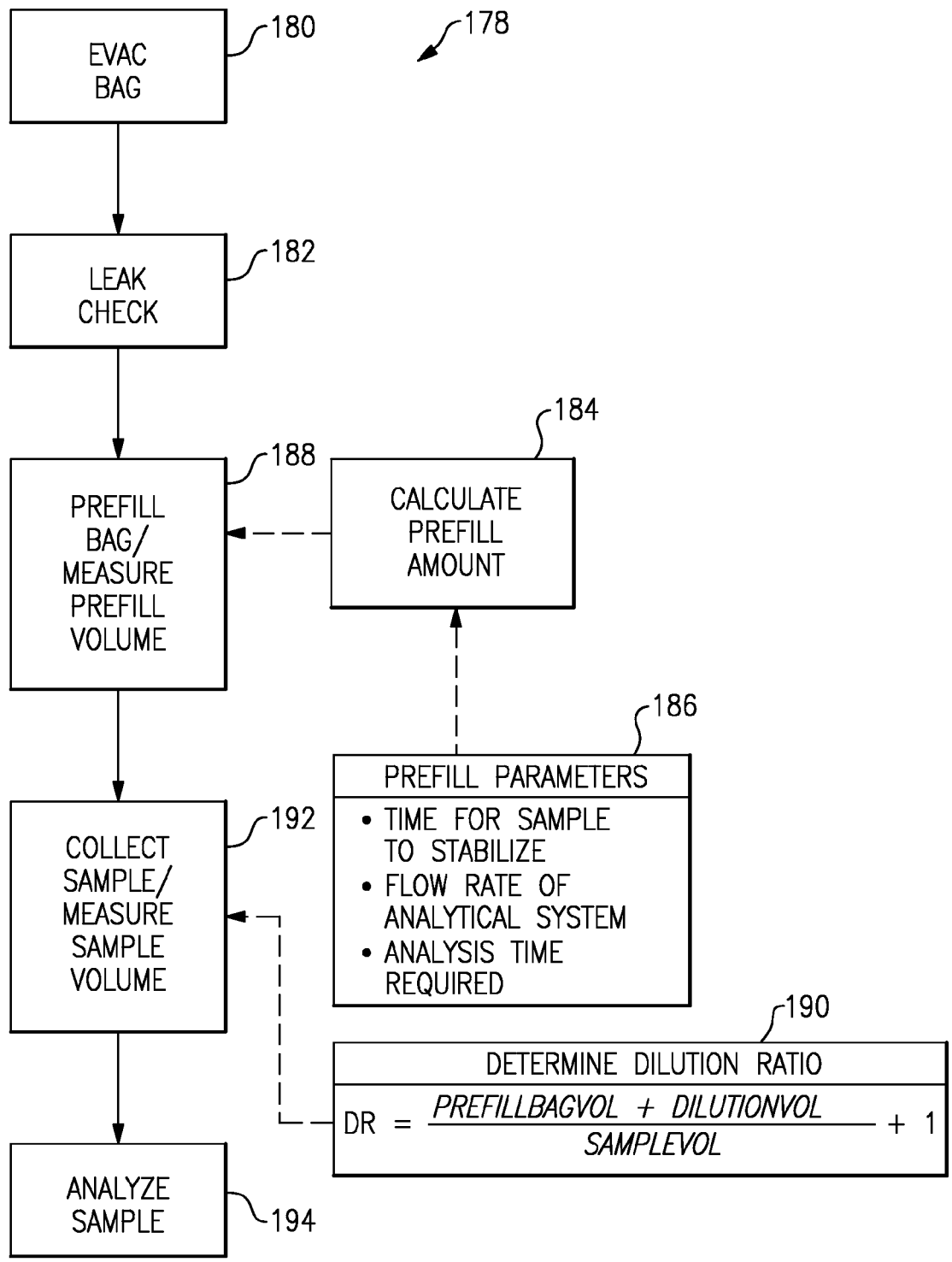
FIG. 4 is a flow chart depicting an example pre-fill procedure.

An example test procedure 178 according to the disclosure is shown in FIG. 4. The amount of pre-fill gas needed to provide a sufficient volume of gases in the bags 152 is calculated at block 184 based upon one or more of the following (indicated at block 186): time for the sample to stabilize (time period for the sample to fully reach the analyzer 160), the flow rate of gases within the analytical system and the analysis time required. In regards to the analysis time required, the amount of sample collected within the bags 152 should be enough to provide the analytical system with approximately 3 minutes of analysis time. This is based upon the typical scenario in which a typical analysis by the analyzer 160 takes approximately 30 seconds to 1 minute. Typically, three or four analyses are conducted with the contents of a given bag 152 in connection with the steps described in relation to block 192. Calculations are performed based upon the various factors of each test to determine the minimum amount of pre-fill gas required for analysis. Pre-filling one or more of the bags 152 is desirable to ensure that enough sample is available for analysis even if the hybrid vehicle produces no exhaust during the sampling period.

The sample bags 152, as well as any intervening conduits, are evacuated through vent 174 using pump 172 (FIG. 3), as indicated at block 180. The system 110 is leak checked (block 182), and the sample bag 152 is filled with a predetermined amount of pre-fill gas, as indicated at block 88. The amount of pre-fill gas is measured. The exhaust sample is collected and its mass and/or volume measured in the sample bag 152 during the test procedure with the pre-fill gas remaining in the sample bag 152, as indicated at block 192.

The collect/measure sample step in block 192 requires a sufficient volume of gases within each sample bag 152 in order to perform the measuring steps. The measuring steps first includes "sniffing" the sample bag 152 to determine the concentration of byproducts that will be analyzed. The analyzer 160 typically includes multiple analyzers, each corresponding to a different concentration range. A particular analyzer having a range corresponding to the "sniffed" range is selected for use in subsequent analysis of each byproduct in the contents of sample bag 152. Secondly, a calibration of the analytical system is performed, including zeroing the instruments, which may be performed by flowing nitrogen through the instruments. Thirdly, an analysis of the contents of the sample bag 152 is then performed to determine the amount of byproducts collected within the bag, such as carbon dioxide, carbon monoxide, hydrocarbons, and oxides of nitrogen. Finally, a zero check is performed to ensure that none of the instruments have drifted during the analysis. Any of the measuring steps above may be repeated if the system fails the calibration check. The system 10 and method 78 shown in FIGS. 1 and 2 also employ the above collect/measure sample step in block 92.

In a typical BMD system, the dilution ratio is measured as the ratio sample flow to total flow of the BMD and integrated over the test procedure. In the example system 110, the dilution ratio integrates the amount of dilution gas in a given bag 152 from the pre-filled process plus the amount of diluent used during the test procedure. The dilution ratio for the system 110 is as follows (block 190):

$$DR = \frac{PrefillBagVol + DilutionVol}{SampleVol} + 1, \qquad \text{Equation 1}$$

where PrefillBagVol, DilutionVol and SampleVol respectively correspond to the pre-fill gas, diluent and sample exhaust gas volumes relating to a given sample bag 152. The contents of the sample bag 152 and ambient bag 142 can then be analyzed to determine the amount of byproducts within the sample, as indicated at block 194. The diluent flow 112 through flow meter 106 may be set to zero, such that the exhaust sample within the bag 152 is only diluted by pre-fill gas 162 within the bag 152 (i.e., Dilution Vol=0).

In one example, the same "zero grade" or "instrument grade" air that is typically used to initially calibrate the system 110 can be used to pre-fill the sample bag 152. As a result, the pre-fill feature can be incorporated into a traditional BMD with very little modification and expense. Alternatively, ambient air can be used to pre-fill the sample bag 152. Using ambient air may be desirable since it makes accounting for the pre-fill air's affects at the analysis stage of the test simpler. The analytical equations set forth in the Code of Federal Regulations for test procedures are such that accounting for pre-fill ambient air is more straightforward. Using zero grade air instead of ambient air requires modifications to those equations, which may be undesired by some customers. It should be understood, however, that any number of suitable substances may be used to pre-fill the sample bags 152.

Although an example embodiment has been disclosed, a worker of ordinary skill in this art would recognize that certain modifications would come within the scope of the claims. For that reason, the following claims should be studied to determine their true scope and content.

What is claimed is:

1. An engine emissions test system comprising:
   a sampling conduit configured to receive a diluted exhaust gas comprising a mixture of make-up gas and exhaust from an engine;
   at least one sample bag configured to store a sample of the diluted exhaust gas;
   a fill circuit configured to communicate the sample of the diluted exhaust gas to the at least one sample bag, the fill circuit including a first gas line having a pump and a flow meter, and the fill circuit further including a second gas line in communication with a fill gas source, the second gas line configured to provide a fill gas to be mixed with the sample of diluted exhaust gas.

2. The system as recited in claim 1, wherein the flow meter of the first gas line is downstream of the pump of the first gas line.

3. The system as recited in claim 2, wherein the first gas line further includes at least one valve between the flow meter of the first gas line and the at least one sample bag.

4. The system as recited in claim 3, wherein the first gas line further includes a valve upstream of the pump of the first gas line.

5. The system as recited in claim 1, wherein the second gas line includes a pump and a flow meter.

6. The system as recited in claim 5, wherein the flow meter of the second gas line is downstream of the pump of the second gas line.

7. The system as recited in claim 6, wherein the second gas line includes a valve between the pump of the second gas line and the flow meter of the second gas line.

8. The system as recited in claim 5, further including a controller connected to the pump in the second gas line and programmed to send a command that provides the at least one sample bag with the fill gas.

9. The system as recited in claim 8, wherein the controller is programmed to provide the at least one sample bag with the fill gas prior to a test procedure.

10. The system as recited in claim 1, wherein the fill gas is ambient air.

11. The system as recited in claim 1, wherein the second gas line is configured to provide the fill gas at a point between the flow meter of the first gas line and the at least one sample bag.

12. The system as recited in claim 1, wherein the first gas line is configured to communicate the sample of diluted exhaust gas between the sampling conduit and the at least one sample bag.

13. The system as recited in claim 12, including a controller, the controller configured to proportionally extract the sample.

14. The system as recited in claim 1, wherein the at least one sample bag is heated to prevent condensation from forming within the at last one sample bag.

* * * * *